United States Patent
Vorozhtsov et al.

(10) Patent No.: US 7,220,425 B2
(45) Date of Patent: May 22, 2007

(54) METHOD FOR THERAPY OF LIVER TUMORS

(75) Inventors: Georgy Nikolaevich Vorozhtsov, Moscow (RU); Eduard Izrailevich Galperin, Moscow (RU); Roman Sergeevich Goloschapov, Moscow (RU); Sergei Vitalievich Grachev, Moscow (RU); Tatyana Gennadievna Dyuzheva, Pavshino (RU); Natalya Ivanovna Kazachkina, Moskovskaya oblast (RU); Oleg Leonidovich Kalia, Moscow (RU); Yury Mikhailovich Luzhkov, Moscow (RU); Evgeny Antonovich Lukyanets, Moscow (RU); Vadim Romanovich Nakhamiyaev, Moscow (RU)

(73) Assignees: Federalnoe Gosudarstvennoe Unitarnoe Predpriyatie Gosudarstvenny Nauchny Tsentr "Nauchno-Issledovatelsky Institut Organicheskikh Poluproduktov I Krasitelei" (FGUP GNTTS "Niopik"), Moscow (RU); Gosudarstevennoe Obrazovatelnoe Uchrezhdenie Vysshego Professionalnogo Obrazovaniya Moskovskaya Meditsinskaya Akademiya IM. I.M. Sechenova RF (Gouvpo MMA IM. I.M. Sechenova MZ RF), Moscow (RU)

( * ) Notice: Subject to any disclaimer, the term of this patent is extended or adjusted under 35 U.S.C. 154(b) by 680 days.

(21) Appl. No.: 10/343,602

(22) PCT Filed: Nov. 26, 2001

(86) PCT No.: PCT/RU01/00505

§ 371 (c)(1),
(2), (4) Date: Jan. 31, 2003

(87) PCT Pub. No.: WO02/45590

PCT Pub. Date: Jun. 13, 2002

(65) Prior Publication Data

US 2003/0166713 A1 Sep. 4, 2003

(30) Foreign Application Priority Data

Dec. 7, 2000 (RU) .............................. 2000130600

(51) Int. Cl.
*A61F 2/06* (2006.01)

(52) U.S. Cl. ..................................................... 424/423
(58) Field of Classification Search ................. 424/423
See application file for complete search history.

(56) References Cited

FOREIGN PATENT DOCUMENTS

RU 1420696 A1 9/1990
RU 2065734 8/1996

OTHER PUBLICATIONS

Liu et al, "Intra-Operative Laser Induced Photodynamic Therapy in the Treatment of Experimental Hepatic Tumors" Abstract, European Journal of gastroenterology & Hepatology, (Nov. 1995), vol. 7, No. 11, pp. 1073-1080.*
Rayner, A.A. et al., "Total hepatic arterial perfusion after occlusion of variant lobar vessels: implications for hepatic arterial chemotherapy", Surgery. Jun. 1986.
Nagasue N. et al. "Hepatic dearterialization for nonrespectable primary and secondary tumors of the liver", Cancer Dec. 1976.
van Hillegersberg, R. et al., "Interstitial photodynamic therapy in a rat liver metastasis model", Cancer, 1992.
Carlsson, G., et al., "Estimation of Liver Tumor Volume Using Different Formulas-An Experimental Study in Rats", Cancer Research Clinical Oncology, 1983, pp. 20-23.
Sofina, E.P., et al., Experimental assessment of antitumor preparations in USSR and USA, 1980, pp. 71-106.

* cited by examiner

*Primary Examiner*—Carlos A. Azpuru
(74) *Attorney, Agent, or Firm*—Winstead PC

(57) ABSTRACT

A method for regional administration of preparations during the therapy of liver tumor, comprising administering a preparation into a branch of the portal vein with the simultaneous occlusion of afferent and efferent lobe vessels (branches of the portal vein proximal the place of puncture, branches of the hepatic artery and lobar hepatic vein) for 5–15 minutes.

During catalytic therapy, it is preferable to use Teraphtalum as the preparation and to administer ascorbic acid after termination of occlusion.

During photodynamic therapy, it is preferable to use photosens as the preparation and to carry out irradiation of the tumor after 10–35 minutes.

This method of administration provides for the predominant accumulation of the preparations in the target lobe (tumor carrier lobe) of the liver, their low penetration into the systemic blood flow, which makes it possible to reduce the dose of the preparation and its general toxicity.

2 Claims, No Drawings

METHOD FOR THERAPY OF LIVER TUMORS

FIELD OF THE INVENTION

The present invention relates to a method for the administration of different preparations into a liver with a tumor lesion and may be utilized in antitumor therapy.

BACKGROUND OF THE INVENTION

A method is known for administration of preparations, on the example of photodynamic therapy of liver tumors, into the hepatic artery (R. van Hillegersberg, J. P. A. Marijnissen, W. J. Kort, P. E. Zondervan, O. T. Terpstra//Interstitial photodynamic therapy in a rat liver metastasis model. Br. J. Cancer, 1992, 66, pp. 1005–1014). Photophrin was used as the preparation and irradiation was carried out 48 hours after its administration.

A drawback of the method is the spread of the preparations into the systemic blood flow, their rapid reduction in the region of damage and as a result—an increase of the general toxicity.

SUMMARY OF THE INVENTION

The object of the invention is to develop a method for administration of preparations to a target lobe (tumor carrier lobe) of the liver, ensuring their predominant accumulation in the target lobe of the liver in combination with a small spread into the systemic blood flow. This makes it possible to reduce the total amount of the introduced preparation and its toxicity.

This object is achieved by introducing a chemical preparation into a branch of the portal vein with the simultaneous occlusion of the afferent (branches of the portal vein proximal the place of puncture and branches of the hepatic artery) and efferent (lobar hepatic vein) vessels of the target lobe of the liver for 5–15 minutes. Thus, direct lengthy contact between the preparation and the target lobe of the liver, which has been eliminated from blood circulation, is accomplished. The indicated method makes it possible during catalytic therapy to introduce a second component of the binary pair—ascorbic acid (AA), immediately after removal of the occlusion with a large content of Teraphtalum (TP) in the target lobe of the liver, and during photodynamic therapy to accomplish irradiation of the tumor in early periods after the administration of a photosensitizer.

DISCLOSURE OF THE INVENTION

Practically speaking, the method is carried out in the following manner. A median laparotomy is conducted, afferent (a branch of the portal vein and hepatic artery) and efferent (a branch of the hepatic vein) vessels of the target lobe of the liver are isolated. They are taken on tourniquets. A puncture of the branch of the portal vein is made, the preparation is introduced therein, simultaneously stopping the flow of blood: the blood inflow—through branches of the portal vein (proximal to the place of puncture) and the hepatic artery, outflow—through a branch of the hepatic vein. Restoration of the blood flow is accomplished by removing clamps from the vessels 5–15 minutes after administration of the preparation.

The following data illustrate the method according to the invention. Teraphtalum (cobalt octacarboxy phthalocyanine) (TP) and Photosens (a mixture of diulfonated, trisulfonated, and tetrasulfonated derivatives of aluminum phthalocyanine) (PS) (GNTs RF "NIOPIK," Moscow) were used as the preparations.

EXAMPLES

1. Study of the Distribution of Teraphtalum with Known Regional and Proposed Methods of Administration.

The studies were carried out on mongrel rats weighing 150 g, obtained from the N. V. Blokhin ONTs breeder and contained in the vivarium of that center.

1.1. Distribution of Teraphtalum in the Case of the Known Regional Administration.

Teraphtalum (TP) was administered once into the general trunk of the portal vein in a dose of 5 mg/kg (this was 1 mg of TP for a rat weighing 200 g). Accumulation of the preparation in the liver, lungs and its level in blood plasma were evaluated by the spectrophotometric method 5, 35 and 240 minutes after the administration.

The results are presented in Table 1. It follows from the table that the kinetics of TP in the case of the known regional administration carried a biexponential character, typical for the systemic intravenous method of administration. The preparation accumulated gradually in the liver and after only 4 hours its concentration fell. A significant amount of TP was detected in the lungs.

TABLE 1

Content of Teraphtalum in blood plasma, liver and lungs of rats with the known regional method of administration in a dose of 5 mg/kg.

| No. | Place of measurement | Content of Teraphtalum ($\mu$g/g of untreated tissue) Time for gathering material after administration of Teraphtalum, min | | |
|---|---|---|---|---|
| | | 5 | 35 | 240 |
| 1 | plasma | 92.4 | 39.6 | 14.4 |
| 2 | liver | 15 | 60 | 51 |
| 3 | lungs | 46 | 28 | 57 |

1.2. Distribution of Teraphtalum in the Case of the Proposed Method for Regional Administration.

Teraphtalum in a dose of 60 or 300 $\mu$g per rat in the form of 0.6 ml of a 0.01 and 0.05% solution was administered into a branch of the portal vein of a target lobe of the liver. The dose of TP introduced by this method is based on the possible volume of the introduced liquid in the target lobe and the allowable concentration of the TP solution which does not cause damage to the endothelium of the vessels.

Thus, the total amount of introduced TP with the proposed method of administering was 3.3 times less (at a concentration of 0.05%) and 16.5 times less (at a concentration of 0.01%) than with the known regional administration (respectively 0.3 mg, 0.06 mg and 1 mg per rat).

Accumulation of the preparation in the target lobe (subjected to occlusion), in the intact lobe of the liver (not subjected to occlusion) and also in the blood plasma were studied 5, 35 and 240 minutes after administration of the preparation by the proposed method. The results are presented in Table 2.

TABLE 2

Content of Teraphtalum in different parts of the liver and plasma of healthy rats with the proposed regional method of administering the preparation in a target lobe of the liver in a dose of 0.3 mg (0.6 ml, 0.01% solution).

| Place of measurement | Content of Teraphtalum (μg/g of untreated tissue) Term of collection of material after administration of Teraphtalum (min) | | |
|---|---|---|---|
| | 5 | 35 | 240 |
| Target lobe of liver | 30 | 33 | 48 |
| Intact lobe of liver | 7 | 5 | 9 |
| Plasma | 3 | — | — |

It is evident from Table 2, that with the proposed method for administration of TP, a rapid accumulation of the preparation in the target lobe of the liver was observed, the difference in the level of the concentration of the preparation in the occluded and intact lobes of the liver was maintained over the whole term of observation—4 hours. The concentration of TP in the target lobe liver in the first minutes after administration by the proposed method was 2 times higher than with the known regional method (see Table 1), while the dose of the introduced TP in the proposed method was 16.5 times less.

The results of a study of the effect of the length of the period of occlusion of the afferent and abducent vessels of the target lobe of the liver on the accumulation of TP therein are presented in Table 3.

TABLE 3

Content of Teraphtalum in blood plasma and different lobes of the liver 35 minutes after administration of the preparation in a dose of 0.3 mg (0.6 ml of a 0.01% solution) by the proposed method depending on the length of the occlusion of the afferent and abducent vessels of the target lobe of the liver.

| No. | Time of occlusion (min) | Place of measurement | Content of Teraphtalum (μg/g) |
|---|---|---|---|
| 1 | 5 | intact lobe | 7 |
| 2 | 15 | of liver | 6 |
| 1 | 5 | target lobe | 35 |
| 2 | 15 | of liver | 35 |
| 1 | 5 | blood plasma | 5 |
| 2 | 15 | | 7 |
| — | control | intact lobe | 17 |
| | | target lobe | 20 |
| | | blood plasma | 6 |

It follows from Table 3 that both with 5 and with 15 minute occlusion of the afferent and abducent vessels of the target lobe of the liver, the content of the preparation was the same in that lobe as in the intact lobe of the liver, i.e. an increase in the time of occlusion did not result in a large accumulation of TP in the target lobe of the liver. At the same time, the selective administration of TP into the lobe branch of the portal vein of the target lobe of the liver without occlusion (control) was accompanied by uniform distribution of the preparation in that lobe and in the intact lobe of the liver: the content of TP 30 minutes after administration was respectively 17 and 20 μg/g, and the level in the plasma—6 μg/g of untreated tissue.

Thus, the proposed regional (selectively-occlusive) method for administration of TP into the target lobe of the liver has advantages over the known regional method, since it ensures predominant accumulation of the preparation in the target lobe of the liver, reduces the total amount of the introduced preparation and its penetration into the systemic blood flow.

1.3. Catalytic Therapy of a Liver Tumor by the "Teraphtalum+Ascorbic Acid" (TP+AA) System when Using the Proposed Method for Administration of Preparations.

The liver tumor was modeled by inoculating into the central lobe of the liver 0.1 ml of a 20% tumoral suspension of a multipassage subcutaneous alveolar mucinous carcinoma of the liver (strain PC-1). Catalytic therapy (CT) was carried out 2 weeks after inoculation of the tumor. TP was administered by the proposed method in a volume of 0.6 ml of a 0.01% solution into a branch of the portal vein of the tumor carrier lobe of the liver with subsequent 5-minute occlusion of afferent and efferent vessels of that lobe, AA (weight ratio to TP–2.2:1) was administered immediately after termination of the occlusion in the same vessel as the TP. Rats with liver tumor, who were not given treatment, served as the control. The results were evaluated 21 days after the treatment. Measurement of the dimensions of the tumor was carried out, the volume of the tumor and the tumor growth inhibition (TGI) index calculated, and also a histological study of the tumor carrier lobe of the liver was carried out.

The volume of the tumor was calculated according to the equation (Carlsson S. R. G., Gullberg B. and Hafstron L. O.//Estimation of liver tumor volume using different formulas—an experimental study in rats. J. Cancer Res. Clin. Oncol. 105, 20–23, 1983):

$$V_{tumor} = (A \times B^2) \times \pi/6$$

$V_{tumor}$ is the volume of the tumor,
A is the maximum diameter of the tumor,
B is the minimum diameter of the tumor,
$\pi = 3.14$.

The tumor growth inhibition index was calculated by the equation (Experimental evaluation of antitumor preparations in USSR and U.S.A., 1980, Moscow, Meditsina, pp. 71–106):

$$TGI(\%) = [(TG_{control} - TG_{test})/TG_{control}] \times 100\%, \text{ where}$$

TGI is the tumor growth inhibition,
$TG_{test}$ is the volume of the tumor (mm$^3$) in rats of the test group,
$TG_{control}$ is the volume of the tumor (mm$^3$) in rats of the control group.

A significant therapeutic effect was considered to be tumor growth inhibition of 50%.

The results of catalytic therapy are presented in Tables 4 and 5.

TABLE 4

Dimensions of liver tumors in rats and data on histological study pf the tumor carrier lobe of liver before and after 21 days after administration of Teraphtalum and ascorbic acid by the proposed method.

| | Dimensions of tumor | |
|---|---|---|
| No. | On 14th day after inoculation of tumor (prior to treatment) | On 35th day after inoculation of tumor (21 days after treatment) |
| 1 | 3 × 3 | 9 × 6 |
| 2 | 2 × 2 | No tumor |
| 3 | 1 × 1 | 3 × 4 |
| 4 | 1 × 1 | No tumor, abscess |
| 5 | 2 × 2 | No tumor, abscess |
| 6 | 2 × 2, 3 × 4 | 7 × 4 |
| 7 | 4 × 2 | 8 × 7 |
| 8 | 7 × 5, 3 × 3 | 8 × 7 |

TABLE 4-continued

Dimensions of liver tumors in rats and data on histological study pf the tumor carrier lobe of liver before and after 21 days after administration of Teraphtalum and ascorbic acid by the proposed method.

| | Dimensions of tumor | |
|---|---|---|
| No. | On 14th day after inoculation of tumor (prior to treatment) | On 35th day after inoculation of tumor (21 days after treatment) |
| Volume of Tumor (mm³) M ± m | 46.8 ± 28.1 | 204.6 ± 67.8 |

\* - the difference between the arithmetical mean indexes of the volume of the tumor before and after action is not reliable, $p > 0.05$.

Two adjacently positioned tumor nodes were detected in a liver lobe in rats No. 6 and No. 8 on the 14th day after inoculation of the tumor.

TABLE 5

Dimensions of liver tumor in rats of control group on the 14th and 35th (corresponding to 21 days after treatment) days after inoculation of the tumor

| | Dimensions of tumor, (mm) | |
|---|---|---|
| No. | on 14th day after inoculation | on 35th day after inoculation |
| 1 | 5 × 4, 2 × 3 | 19 × 7 |
| 2 | 3 × 4 | 7 × 3, 7 × 4 |
| 3 | 6 × 9, 6 × 4 | 5 × 12, 6 × 10, 6 × 10, 5 × 12 |
| 4 | 5 × 2 | 12 × 2, 1 × 2, 2 × 2 |
| 5 | 3 × 4 | 4 × 4, 10 × 7 |
| 6 | 3 × 4 | 4 × 5, 3 × 4, 7 × 6 |
| 7 | 5 × 5 | 20 × 13, 10 × 7 |
| 8 | 5 × 4 | 20 × 20 |
| Volume of tumor (mm³)M ± m | 86.07 ± 36.3 | 1489.2 ± 760* |

*the difference between the arithmetical mean indexes of the volume of the tumor on 14th and 35th days after inoculation of the tumor suspension is reliable, $p < 0.05$.

Two adjacently positioned tumor nodes were detected in a liver lobe in rats No. 1 and No. 3 on the 14th day after inoculation of the tumor.

From 2 to 4 tumor nodes were detected in rats No. 2–7 on the 21st day after treatment (35 days after inoculation of the tumor) in a lobe of the liver.

It was determined during a comparative analysis of the results in the main and control groups (see Tables 4 and 5) that prior to treatment (14 days after inoculation of the tumor) the dimensions of the tumors were comparable and were 46.8±28.1 and 86.1±36.3 mm³, respectively (p>0.05).

In the group of animals who were given treatment in accordance with the proposed method (see Table 4), tumor carrier lobes of malignant cells were not detected in 3 out of 8 rats during a histological study, in the other 5 animals there was not a reliable increase of the tumor: 46.8±28.1 mm³ (prior to treatment) and 204.6±67.8 mm³ (after treatment), p>0.05.

In the control group (see Table 5) the size of the tumors 35 days after the inoculation was reliably greater than in the test group: 1489.2±760 mm³ and 204.6±67.8 mm³, p<0.05.

The TGI index on the 21st day after treatment (35 days after inoculation of the tumor) was 86.3% with use of the proposed method for administration of preparations of a catalytic binary pair.

II. Study of the Distribution of Photosensitizer with the Proposed Method for Administration.

A photosens (PS) (GNTs "NIOPIK," Moscow) was used as the photosensitizer. Studies were carried out on mongrel rats weighing 150 g, obtained from the "Stolbovaya" nursery and kept in the P. A. Gertsen MNIOI vivarium. The photosens was administered in a dose of 1 mg/kg systemically intravenously (group 1) and in accordance with the proposed method (group 2). Distribution of the PS in the tissues was studied with the aid of specific fluorescence by a contact method on a "Spektr" (TOO "Klaster") laser diagnostic installation. Normalized fluorescence (NF) was determined 5, 15, 35 minutes and 24 hours after administration of the preparation. The results are presented in Tables 6 and 7. It follows from Table 6 that with systemic intravenous administration (group 1) the PS was distributed uniformly in the central (target lobe) and upper lateral (intact) lobes of the liver. A rapid accumulation of the preparation in the skin was noted.

During the administration of the preparation by the proposed method (group 2) with subsequent occlusion, a reliable difference between the NF in the indicated lobes of the liver was noted: the content of PS in the target lobe was higher as compared with the intact lobe. Wherein, the content of PS in the skin of rats of group 2 was lower than in the animals of group 1. These differences were maintained for 35 minutes after the administration of the preparation, by 24 hours the difference leveled out, which probably was related to the removal of PS from the occluded lobe of the liver.

When PS is administered by the proposed method to rats with liver tumor, the main accumulation of PS in the tumor and the parenchyma surrounding the tumor carrier lobe of the liver in the early period after administration is also noted (see Table 7).

TABLE 6

Indexes of normalized fluorescence of photosens in different lobes of the liver and skin of healthy rats with the proposed and systemic intravenous administration of the preparation.

| | | Indexes of normalized fluorescence, (c.u.) Place of measurement (lobe of liver) | | | |
|---|---|---|---|---|---|
| Time of study after administration of preparation | Method of administration of photosens | Central (target lobe) | Upper (intact) | Right lateral (intact) | Skin |
| 5 minutes | Proposed | 141.2 ± 44.8 | 55.6 ± 2.1* | 76.2 ± 17.1 | 6.9 ± 1.2* |
| | Systemic intravenous | 112.6 ± 6.8 | 119.5 ± 11.9 | 113.1 ± 8.4 | 15.2 ± 0.9 |

TABLE 6-continued

Indexes of normalized fluorescence of photosens in different lobes of the liver and skin of healthy rats with the proposed and systemic intravenous administration of the preparation.

| Time of study after administration of preparation | Method of administration of photosens | Indexes of normalized fluorescence, (c.u.) Place of measurement (lobe of liver) | | | |
|---|---|---|---|---|---|
| | | Central (target lobe) | Upper (intact) | Right lateral (intact) | Skin |
| 15 minutes | Proposed | 157.0 ± 39.4 | 70.0 ± 4.6* | 76.7 ± 17.8 | 10.5 ± 1.1* |
| | Systemic intravenous | 118.3 ± 8.6 | 106.4 ± 8.6 | 111.5 ± 6.7 | 19.8 ± 3.6 |
| 35 minutes | Proposed | 165.1 ± 39.7 | 99.5 ± 7.9* | 91.4 ± 8.9 | 11.3 ± 0.5* |
| | Systemic intravenous | 114.0 ± 5.9 | 122.0 ± 4.6 | 106.0 ± 3.9 | 21.8 ± 3.8 |
| 24 hours | Proposed | 79.9 ± 46.3 | 117.5 ± 6.1 | 99.9 ± 7.2* | 17.6 ± 2.3 |
| | Systemic intravenous | 133.9 ± 3.8 | 138.6 ± 9.7 | 134.2 ± 2.0 | 18.4 ± 0.3 |

*reliability of the difference of the indexes in an identical lobe of the liver and skin with systemic intravenous and the proposed methods of administration, $p < 0.05$.

TABLE 7

Indexes of normalized fluorescence of photosens in the tumor, the parenchyma surrounding the liver tumor, and skin of rats with the proposed and systemic intravenous administration of the photosensitizer in a dose of 1 mg/kg.

| Place of measurement | Method of administration | Indexes of normalized fluorescence, (c.u.) Time of measurement after administration of PS | | | |
|---|---|---|---|---|---|
| | | 5 min | 15 min | 35 min | 24 hours |
| Liver tumor | Proposed | 84 ± 19 | 88 ± 9 | 113 ± 24 | — |
| | Systemic intravenous | 46.1 ± 5.5 | 65.4 ± 7.4 | 70.0 ± 6.1 | 93.4 ± 9.3 |
| Parencyma surrounding liver tumor | Proposed | 161.5 ± 39.7 | 178.9 ± 15.2 | 148.2 ± 20.3 | — |
| | Systemic intravenous | 111.2 ± 6.4 | 116.6 ± 5.2* | 117.1 ± 3 | 119 ± 3 |
| Skin | Proposed | 10.0 ± 1.2 | 8.5 ± 0.9 | 10.7 ± 1.6 | — |
| | Systemic intravenous | 11.2 ± 2 | 14.5 ± 6 | 13.2 ± 2.1 | 14 ± 1 |

*reliability of difference of indexes of normalized fluorescence of photosens in corresponding tissues with different methods of administration of the photosens, $p < 0.05$.

PDT in both groups was carried out with identical parameters of irradiation: power of 200 mW/cm², light dose of 150 J/cm². After 3 days the animals were killed, the tumor carrier lobe of the liver was sent for histological study, which showed that in rats of group 1, ⅓ of the area of the tumor remained the same, while in animals of group 2, total necroses of tumor nodes was noted.

The results of PDT were studied on the 21st day after irradiation of the tumor. The test group was composed of rats who were subjected to irradiation after the administration of photosens by the proposed method. The control group was composed of animals in which after 2 weeks after inoculation of the tumor the size of the tumor was measured during laparotomy, and PDT was not carried out. The results of PDT are presented in FIG. 1.

It is evident from FIG. 1 that 2 weeks after inoculation, the size of the tumors in the control and test groups did not reliably differ, being respectively 45.6±16.5 and 76.9±29.5 mm³, p>0.05. On the 21st day the size of the tumor in the control group reliably increased to 397.04±41.7 mm³, p<0.05. A reliable increase of the size of the tumor in the test group was not noted, the area of the tumor was 57.2±25.03 mm³, p>0.05. After the PDT, tumor growth inhibition was 81.3%.

Thus, the proposed method for administration of the preparations as compared with the known method ensures their advantageous accumulation in the target lobe (tumor carrier lobe) of the liver, small penetration into the systemic blood flow, which makes it possible to reduce the dose of the preparation and its general toxicity.

The invention claimed is:

1. A method of catalytic therapy of a liver tumor comprising:
    occluding afferent and efferent vessels of a target lobe of the liver for 5–15 minutes; and
    administering a cobalt octacarboxy phthalocyanine preparation into a portal vein of the target lobe of the liver (tumor carrier lobe) during occlusion.

2. A method of photodynamic therapy of a liver tumor comprising:
    occluding afferent and efferent vessels of a target lobe of the liver for 5–15 minutes; and
    administering a preparation comprising a mixture of disulfonated, trisulfonated, and tetrasulfonated derivatives of aluminum phthalocyanine into a portal vein of the target lobe of the liver (tumor carrier lobe) during occlusion.

* * * * *

UNITED STATES PATENT AND TRADEMARK OFFICE
CERTIFICATE OF CORRECTION

PATENT NO. : 7,220,425 B2  Page 1 of 1
APPLICATION NO. : 10/343602
DATED : May 22, 2007
INVENTOR(S) : Georgy Nikolacvich Vorozhtsov et al.

It is certified that error appears in the above-identified patent and that said Letters Patent is hereby corrected as shown below:

COLUMN 1, LINE 67

Replace "diulfonated"
With --disulfonated--

Signed and Sealed this

Second Day of September, 2008

JON W. DUDAS
*Director of the United States Patent and Trademark Office*